United States Patent
Dekker

(10) Patent No.: US 8,687,472 B1
(45) Date of Patent: Apr. 1, 2014

(54) METHOD AND APPARATUS FOR DETERMINING THE CLEANLINESS OF A LENS IN AN OPTICAL DISC DRIVE

(71) Applicant: Marvell International Ltd., Hamilton (BM)

(72) Inventor: Antonius Leonardus Johannes Dekker, Eindhoven (NL)

(73) Assignee: Marvell International Ltd., Hamilton (BM)

( * ) Notice: Subject to any disclaimer, the term of this patent is extended or adjusted under 35 U.S.C. 154(b) by 0 days.

(21) Appl. No.: 13/670,936

(22) Filed: Nov. 7, 2012

Related U.S. Application Data

(60) Provisional application No. 61/557,315, filed on Nov. 8, 2011.

(51) Int. Cl.
  *G11B 7/00* (2006.01)
  *G11B 7/1372* (2012.01)
  *G11B 7/09* (2006.01)
  *G01N 21/94* (2006.01)

(52) U.S. Cl.
  CPC ............ *G11B 7/1372* (2013.01); *G11B 7/0917* (2013.01); *G11B 7/0948* (2013.01); *G01N 21/94* (2013.01)
  USPC ..................................... 369/53.12; 369/53.25

(58) Field of Classification Search
  CPC .. G11B 7/1372; G11B 7/0917; G11B 7/0948; G01N 21/94
  See application file for complete search history.

(56) References Cited

U.S. PATENT DOCUMENTS

| | | | | |
|---|---|---|---|---|
| 4,750,163 A | * | 6/1988 | Yamamiya et al. | 369/53.12 |
| 5,210,735 A | * | 5/1993 | Hoshino et al. | 369/53.13 |
| 5,390,160 A | * | 2/1995 | Sasaki | 369/53.12 |
| 5,471,451 A | * | 11/1995 | Masaki et al. | 369/71 |
| 6,424,606 B1 | * | 7/2002 | Okazaki et al. | 369/44.32 |
| 6,449,232 B1 | * | 9/2002 | Kuwahara et al. | 369/53.23 |
| 6,606,284 B1 | * | 8/2003 | Sakamoto et al. | 369/44.29 |
| 2004/0004913 A1 | * | 1/2004 | Wada et al. | 369/44.32 |
| 2004/0062164 A1 | * | 4/2004 | Miyamoto et al. | 369/53.26 |
| 2004/0139457 A1 | * | 7/2004 | Kobayashi | 720/718 |
| 2007/0025215 A1 | * | 2/2007 | Kinoshita et al. | 369/53.15 |
| 2012/0020197 A1 | * | 1/2012 | Matsuda et al. | 369/100 |

FOREIGN PATENT DOCUMENTS

| | | | | | |
|---|---|---|---|---|---|
| JP | 61248242 A | * | 11/1986 | | G11B 7/12 |
| JP | 62173629 A | * | 7/1987 | | G11B 7/00 |
| JP | 62184637 A | * | 8/1987 | | G11B 7/135 |
| JP | 02239435 A | * | 9/1990 | | G11B 7/125 |
| JP | 02278530 A | * | 11/1990 | | G11B 7/12 |
| JP | 04098626 A | * | 3/1992 | | G11B 7/125 |
| JP | 05135395 A | * | 6/1993 | | G11B 7/12 |

* cited by examiner

*Primary Examiner* — Peter Vincent Agustin

(57) ABSTRACT

Apparatus having corresponding methods comprise: a light source configured to produce light; a lens configured to focus the light on an optical disc; a photo detector configured to obtain a measurement of the light reflected by the optical disc; and a controller configured to determine a cleanliness of the lens based on the measurement of the light reflected by the optical disc responsive to the lens focusing the light on a surface of the optical disc.

16 Claims, 3 Drawing Sheets

METHOD AND APPARATUS FOR DETERMINING THE CLEANLINESS OF A LENS IN AN OPTICAL DISC DRIVE

CROSS-REFERENCE TO RELATED APPLICATIONS

This disclosure claims the benefit of U.S. Provisional Patent Application Ser. No. 61/557,315, filed on Nov. 8, 2011, entitled "Lens dust detector," the disclosure thereof incorporated by reference herein in its entirety.

FIELD

The present disclosure relates generally to the field of optical disc drives. More particularly, the present disclosure relates to contamination of a lens of an optical disc drive.

BACKGROUND

The lens in an optical disc drive focuses light on the data layer of an optical disc. The reflected light passes through the lens and is sensed by a photo detector, which provides corresponding electronic signals that are processed to provide output signals such as audio and video signals. With time and use, the lens becomes contaminated. For example, dust, hair, lint, smoke residue, and the like (collectively referred to herein as "dust") accumulates on the lens. This dust causes diffusion of the light, causing less light to reach the photo detector. As a result, the optical disc drive experiences playback problems such as skipping and freezing, as well as reduced quality of the output signals.

SUMMARY

In general, in one aspect, an embodiment features an apparatus comprising: a light source configured to produce light; a lens configured to focus the light on an optical disc; a photo detector configured to obtain a measurement of the light reflected by the optical disc; and a controller configured to determine a cleanliness of the lens based on the measurement of the light reflected by the optical disc responsive to the lens focusing the light on a surface of the optical disc.

Embodiments of the apparatus can include one or more of the following features. In some embodiments, the measurement of the light reflected by the optical disc represents a power of the light reflected by the optical disc. In some embodiments, the controller is further configured to determine the cleanliness of the lens based on a power of the light produced by the light source.

In general, in one aspect, an embodiment features a method comprising: causing a lens to focus a light on a surface of an optical disc; obtaining a measurement of the light reflected by the optical disc responsive to the lens focusing the light on the surface of the optical disc; and determining a cleanliness of the lens based on the measurement of the light reflected by the surface of the optical disc.

Embodiments of the method can include one or more of the following features. Some embodiments comprise indicating the cleanliness of the lens.

In general, in one aspect, an embodiment features a controller configured to perform functions comprising: causing a light source of an optical disc drive to produce light; causing a lens of the optical disc drive to focus the light on a surface of an optical disc; obtaining a measurement of the light reflected by the optical disc responsive to the lens focusing the light on the surface of the optical disc; and determining a cleanliness of the lens based on the measurement of the light reflected by the surface of the optical disc.

The details of one or more implementations are set forth in the accompanying drawings and the description below. Other features will be apparent from the description and drawings, and from the claims.

Figure 1:
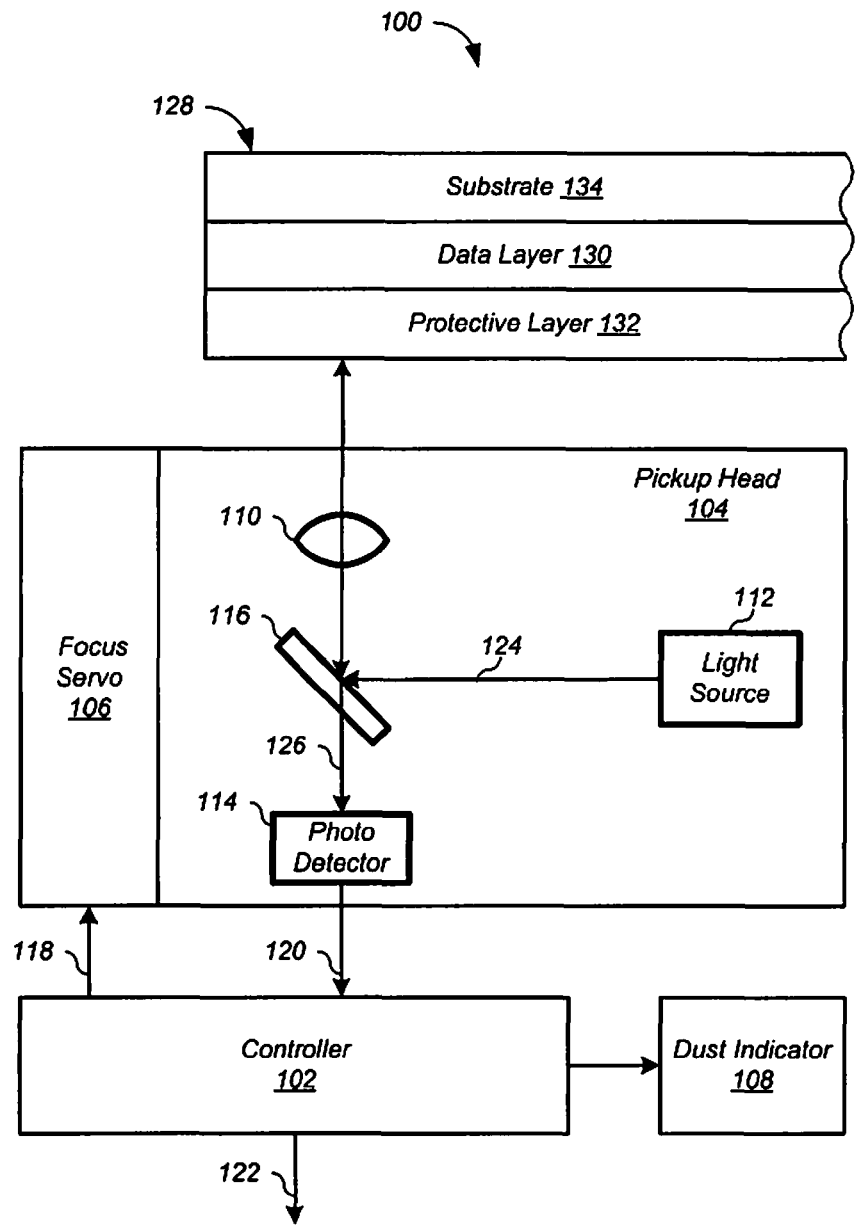
FIG. 1 is a simplified diagram of a portion of an optical disc drive according to one embodiment.

The leading digit(s) of each reference numeral used in this specification indicates the number of the drawing in which the reference numeral first appears.

DETAILED DESCRIPTION

Embodiments of the present disclosure provide lens dust detection for optical disc drives. Put another way, these embodiments determine a cleanliness of the lens in an optical disc drive by using a light source of the optical disc drive to detect dust on the lens of the optical disc drive. Moreover, "blue" light, such as that produced by a 450 nm laser, is particularly useful for such lens dust detection. According to the described embodiments, the dust can be detected when the lens is focused on the surface of the disc. In this description, the term "surface" is used to describe the interface between the air and the protective layer of an optical disc. The light reflection from the surface of an optical disc is fairly constant for all discs. And because the amount of reflected light decreases as the amount of dust increases, the amount of reflected light can be used to indicate the amount of dust on the lens.

FIG. 1 is a simplified diagram of a portion of an optical disc drive 100 according to one embodiment. Although in the described embodiments the elements of optical disc drive 100 are presented in one arrangement, other embodiments may feature other arrangements. For example, elements optical disc drive 100 can be implemented in hardware, software, or combinations thereof. The described optical disc drives can also be implemented as optical disc burners, optical disc players, and the like.

Referring to FIG. 1, optical disc drive 100 includes a controller 102, a pickup head 104, a focus servo 106, and a dust indicator 108. The controller 102 can be implemented as a processor. Processors according to various embodiments can be fabricated as one or more integrated circuits.

The pickup head 104 includes a lens 110, a light source 112, a photo detector 114, and a mirror 116. In operation, the controller 102 generates control signals 118 that cause the focus servo 106 to move the pickup head 104 so that the lens 110 focuses onto an optical disc 128. The light source 112 produces light 124. The mirror 116 reflects the light 124 from the light source 112 to the lens 110, and passes the light 126 reflected from the optical disk 128 to the photo detector 114. Based on the reflected light 126, the photo detector 114 provides electronic signals 120 to the controller 102. The controller 102 processes the electronic signals 120 to provide output signals 122 such as audio and video signals, data signals, and the like.

According to one embodiment, the light source 112 is implemented as one or more lasers. The lasers 112 include a "blue" laser such as those used in some DVD players. Note that even though the laser 112 is called "blue," its color is actually in the violet range. That is, the wavelength of the light produced by the blue laser 112 is approximately 405 nm. The lasers 112 can also include a 650 nm red laser such as those used in some DVD players, a 780 nm infrared laser such as those used in CD players, and the like.

The optical disc drive 100 supports an optical disc 128. The optical disc 128 includes a data layer 130, a protective layer 132, and a substrate 134. The substrate 134 is generally implemented as a polycarbonate layer. In some optical discs 128 such as CDs and DVDs, the protective layer 132 is implemented as a polycarbonate substrate. In other optical discs 128 such as some DVDs and CDs, the protective layer 132 is implemented as a protective coating. The data layer 130 includes pits and lands that represent data. The pits and lands have different reflectivity, which the photo detector 114 employs to generate the electronic signals 120.

Figure 2:
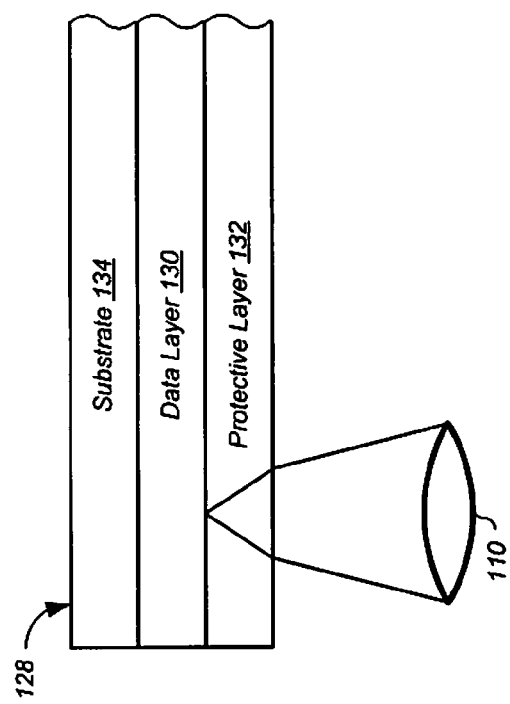
FIG. 2 illustrates the spatial relationship between the lens and the optical disc of FIG. 1 during playback.

FIG. 2 illustrates the spatial relationship between the lens 110 and the optical disc 128 of FIG. 1 during playback. During playback, the pickup head 104 is positioned so that the lens 110 is focused on the data layer 130 of the optical disc 128. The controller 102 and the focus servo 106 closely maintain this spatial relationship throughout playback.

Figure 3:
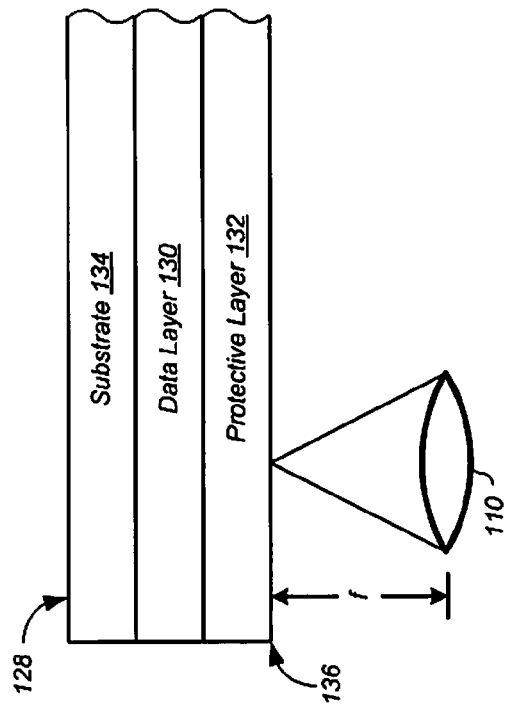
FIG. 3 illustrates the spatial relationship between the lens and the optical disc of FIG. 1 during a lens dust measurement according to one embodiment.

FIG. 3 illustrates the spatial relationship between the lens 110 and the optical disc 128 of FIG. 1 during a lens dust measurement according to one embodiment. During the lens dust measurement, the pickup head 104 is positioned so that the lens 110 is focused on the surface 136 of the optical disc 128. That is, the distance between the center of the lens 110 and the surface 136 of the optical disc 128 is the focal length f of the lens 110. This spatial relationship can be attained in any manner.

In conventional optical disc drives, before playback begins, the pickup head 104 seeks the data layer 130 of the optical disc 128. During loading of the optical disc 128 into the optical disc drive 100, the controller 102 causes the focus servo 106 to keep the pickup head 104 far from the optical disc 128 to avoid damage. When playback is initiated, for example when a user pushes the "play" button of the optical disc drive 100, the seek process begins. In this seek process, the controller 102 causes the focus servo 106 to move the pickup head 104 toward the optical disc 128 until the lens 110 is focused on the data layer 130 of the optical disc 128. During this movement, the focal point of the lens 110 passes through the surface 136 of the optical disc, as shown in FIG. 3. The dust measurement is obtained at that time. Alternatively, the controller 102 can cause the focus servo 106 to move the pickup head 104 to the position of FIG. 3 at any time in order to obtain the dust measurement.

Figure 4:
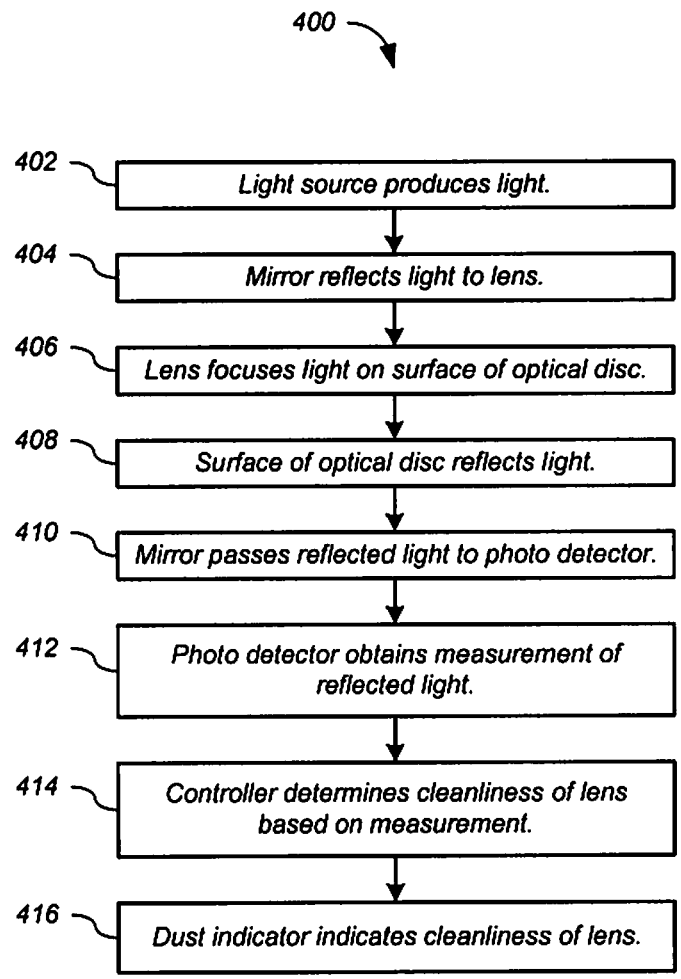
FIG. 4 shows a dust measurement process for the optical disc drive of FIG. 1 according to one embodiment.

FIG. 4 shows a dust measurement process 400 for the optical disc drive 100 of FIG. 1 according to one embodiment. Although in the described embodiments the elements of process 400 are presented in one arrangement, other embodiments may feature other arrangements. For example, in various embodiments, some or all of the elements of process 400 can be executed in a different order, concurrently, and the like. Also some elements of process 400 may not be performed, and may not be executed immediately after each other. In addition, some or all of the elements of process 400 can be performed automatically, that is, without human intervention.

Referring to FIG. 4, at 402, the light source 112 produces light 124. At 404, the mirror 116 reflects the light 124 to the lens 110. At 406, the lens 110 focuses the light on the surface 136 of the optical disc 128. At 408, the surface 136 of the optical disc 128 reflects the light 124 as reflected light 126. At 410, the mirror 116 passes the reflected light 126 to the photo detector 114. At 412, the photo detector 114 obtains a measurement (electronic signals 120) of the light 126 reflected by the optical disc 128. At 414, the controller 102 determines a cleanliness of the lens 110 based on the measurement of the light 126 reflected by the optical disc 128 responsive to the lens 110 focusing the light on the surface of the optical disc 128. At 416, the dust indicator 108 indicates the cleanliness of the lens 110. The dust indicator can be implemented, for example, as an LED on the front panel of the optical disc drive 100.

The controller 102 can determine the cleanliness of the lens 110 based on the reflected light 126 by any means. In some embodiments, the measurement of the light 126 reflected by the optical disc 128 represents the power of the light 126 reflected by the optical disc 128. In some embodiments, the controller 102 determines the cleanliness of the lens 110 by comparing the power of the light 126 reflected by the optical disc 128 to the power of the light 124 produced by the light source 112. In some embodiments, the controller 102 determines the cleanliness of the lens 110 based on a calibration value, where the calibration value represents a measurement of the light 126 reflected when the lens 110 is clean. Other embodiments can employ any combination of the above techniques.

As mentioned above, different types of optical discs 128 implement the protective layer 132 with different materials. In some embodiments, the dust measurement process accounts for these differences. In such embodiments, the optical disc drive 100 first determines the type of optical disc 128 present in the optical disc drive 100, for example using conventional techniques. The optical disc drive 100 then modifies the measurement process according to the type of protective layer 132 used in that type of optical disc 128. For example, the controller 102 can employ a respective reflection coefficient for each type of optical disc 128.

In some embodiments, the optical disc drive 100 is implemented as a stand-alone unit such as an optical disc player or the like. In other embodiments, the optical disc drive 100 is implemented as part of a computer system. For example, the optical disc drive 100 can be installed in a personal computer or the like. In such embodiments, the computer can request the cleanliness of the lens 110, for example by issuing an ATA Packet Interface (ATAPI) command. The response to the command can be the percentage of light reduction compared with a clean optical disc 128.

Various embodiments of the present disclosure can be implemented in digital electronic circuitry, or in computer hardware, firmware, software, or in combinations thereof. Embodiments of the present disclosure can be implemented in a computer program product tangibly embodied in a computer-readable storage device for execution by a programmable processor. The described processes can be performed by a programmable processor executing a program of instructions to perform functions by operating on input data and generating output. Embodiments of the present disclosure can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, processors receive instructions and data from a read-only memory and/or a random access memory. Generally, a computer includes one or more mass storage devices for storing data files. Such devices include magnetic disks, such as internal hard disks and removable disks, magneto-optical disks; optical disks, and solid-state disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

A number of implementations have been described. Nevertheless, various modifications may be made without departing from the scope of the disclosure. Accordingly, other implementations are within the scope of the following claims.

What is claimed is:

1. An apparatus comprising:
a light source configured to produce light;
a lens configured to focus the light on an optical disc, wherein the lens is configured to i) focus on a data layer of the optical disc while in a first position relative to the optical disc, and ii) focus on an outer surface of the optical disc while in a second position relative to the optical disc, wherein
the first position is a first distance from the outer surface of the optical disc, and
the second position is a second distance from the outer surface of the optical disc that is different from the first distance;
a photo detector configured to obtain a measurement of the light reflected by the optical disc while the lens is in the second position; and
a controller configured to i) control movement of the lens to the second position to focus the lens on the outer surface of the optical disc, and ii) determine a cleanliness of the lens based on the measurement of the light reflected by the optical disc while the lens is focusing the light on the outer surface of the optical disc.

2. The apparatus of claim 1, wherein:
a wavelength of the light produced by the light source is approximately 405 nm.

3. The apparatus of claim 1, wherein:
the measurement of the light reflected by the optical disc represents a power of the light reflected by the optical disc.

4. The apparatus of claim 3, wherein:
the controller is further configured to determine the cleanliness of the lens based on the power of the light produced by the light source.

5. The apparatus of claim 1, wherein:
the controller is further configured to determine the cleanliness of the lens based on a calibration value, wherein the calibration value represents another measurement of the light reflected when the lens is clean.

6. The apparatus of claim 1, further comprising:
a dust indicator configured to indicate the cleanliness of the lens.

7. An optical disc drive comprising the apparatus of claim 1.

8. An optical disc player comprising the optical disc drive of claim 7.

9. The apparatus of claim 1, wherein the second position corresponds to a focal length of the lens relative to the outer surface of the optical disc.

10. A method, comprising:
causing a lens to focus a light on an optical disc including a data layer and an outer surface, wherein the lens focuses the light on the data layer while in a first position relative to the optical disc, and the lens focuses the light on the outer surface while in a second position relative to the optical disc, wherein
the first position is a first distance from the outer surface of the optical disc, and
the second position is a second distance from the outer surface of the optical disc that is different from the first distance;
obtaining a measurement of the light reflected by the outer surface of the optical disc while the lens is i) in the second position and ii) focusing the light on the outer surface of the optical disc; and
determining a cleanliness of the lens based on the measurement of the light reflected by the outer surface of the optical disc.

11. The method of claim 10, wherein:
a wavelength of the light produced by a light source is approximately 405 nm.

12. The method of claim 10, wherein:
the measurement of the light reflected by the optical disc represents a power of the light reflected by the optical disc.

13. The method of claim 12, further comprising:
determining the cleanliness of the lens based on the power of the light produced by a light source.

14. The method of claim 10, further comprising:
determining the cleanliness of the lens based on a calibration value, wherein the calibration value represents another measurement of the light reflected when the lens is clean.

15. The method of claim 10, further comprising:
indicating the cleanliness of the lens.

16. The method of claim 10, wherein the second position corresponds to a focal length of the lens relative to the outer surface of the optical disc.

* * * * *